(12) United States Patent
Mansour et al.

(10) Patent No.: US 8,074,964 B2
(45) Date of Patent: Dec. 13, 2011

(54) LUER ACTIVATED MEDICAL CONNECTOR HAVING A LOW PRIMING VOLUME

(75) Inventors: George Michel Mansour, Pomona, CA (US); Tim L. Truitt, Orange, CA (US)

(73) Assignee: CareFusion 303, Inc., San Diego, CA (US)

( * ) Notice: Subject to any disclaimer, the term of this patent is extended or adjusted under 35 U.S.C. 154(b) by 567 days.

(21) Appl. No.: 12/204,941

(22) Filed: Sep. 5, 2008

(65) Prior Publication Data
US 2010/0059702 A1    Mar. 11, 2010

(51) Int. Cl.
*F16K 51/00*    (2006.01)
(52) U.S. Cl. .................................. 251/149.7; 251/149.3
(58) Field of Classification Search .............. 251/149.1, 251/149.3, 149.6, 149.7
See application file for complete search history.

(56) References Cited

U.S. PATENT DOCUMENTS

| | | | | |
|---|---|---|---|---|
| 4,683,916 A | * | 8/1987 | Raines | 137/854 |
| 5,360,413 A | * | 11/1994 | Leason et al. | 604/249 |
| 5,569,235 A | | 10/1996 | Ross et al. | |
| 5,578,059 A | * | 11/1996 | Patzer | 604/249 |
| 5,730,418 A | | 3/1998 | Feith et al. | |
| 6,482,188 B1 | | 11/2002 | Rogers et al. | |
| 2004/0158210 A1 | | 8/2004 | Staunton et al. | |
| 2008/0103482 A1 | | 5/2008 | Fangrow | |
| 2008/0169444 A1 | | 7/2008 | Guala | |
| 2008/0215014 A1 | | 9/2008 | Nordgren | |

FOREIGN PATENT DOCUMENTS

| | | |
|---|---|---|
| DE | 43 11 715 A1 | 10/1994 |
| EP | 0 471 547 A1 | 2/1992 |
| WO | WO 2006/062912 A1 | 6/2006 |

OTHER PUBLICATIONS

International Search Report and the Written Opinion issued for PCT/US2009/055732, dated Nov. 13, 2009, 8 pages.
Supplementary European Search Report for EP 09 81 2166 dated Aug. 11, 2011 in 6 pages.

* cited by examiner

*Primary Examiner* — John Fristoe, Jr.
(74) *Attorney, Agent, or Firm* — McDermott Will & Emery LLP

(57) ABSTRACT

A connector is described which includes a valve housing comprising a valve housing base and a valve cap, the valve housing defining an inlet port, and an outlet port, the valve housing further including a fluid path from the inlet port to the outlet port, the fluid path including a channel formed in an inner wall of the valve housing. A valve insert in the valve housing defines a bowl sealed by a diaphragm, such that the sealed bowl forms an inner volume in the valve housing. A valve plug operable seals the inlet port when the connector is in an unactuated state thereby closing the fluid path through the connector. Upon actuation of the connector the valve plug deforms the diaphragm into the inner volume thereby unsealing the inlet port and opening the fluid path through the connector. Because of the arrangement of the valve plug, valve insert and diaphragm, the connector has a low priming volume and has positive fluid displacement characteristics upon actuation.

8 Claims, 5 Drawing Sheets

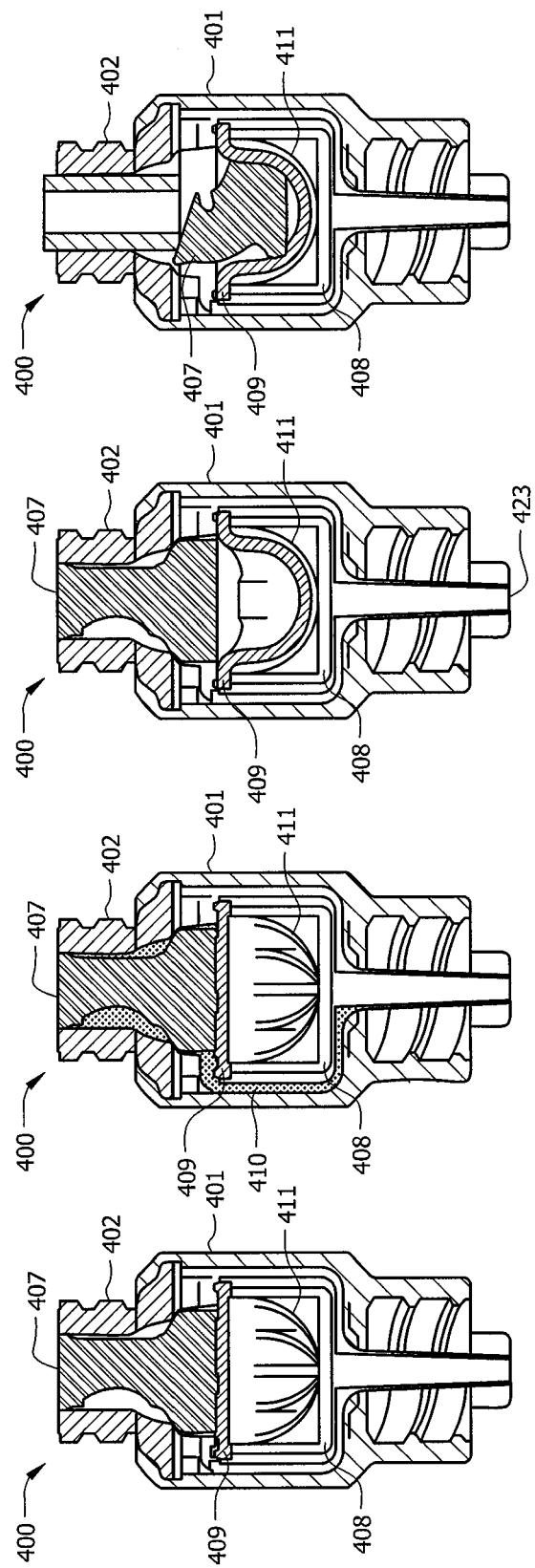

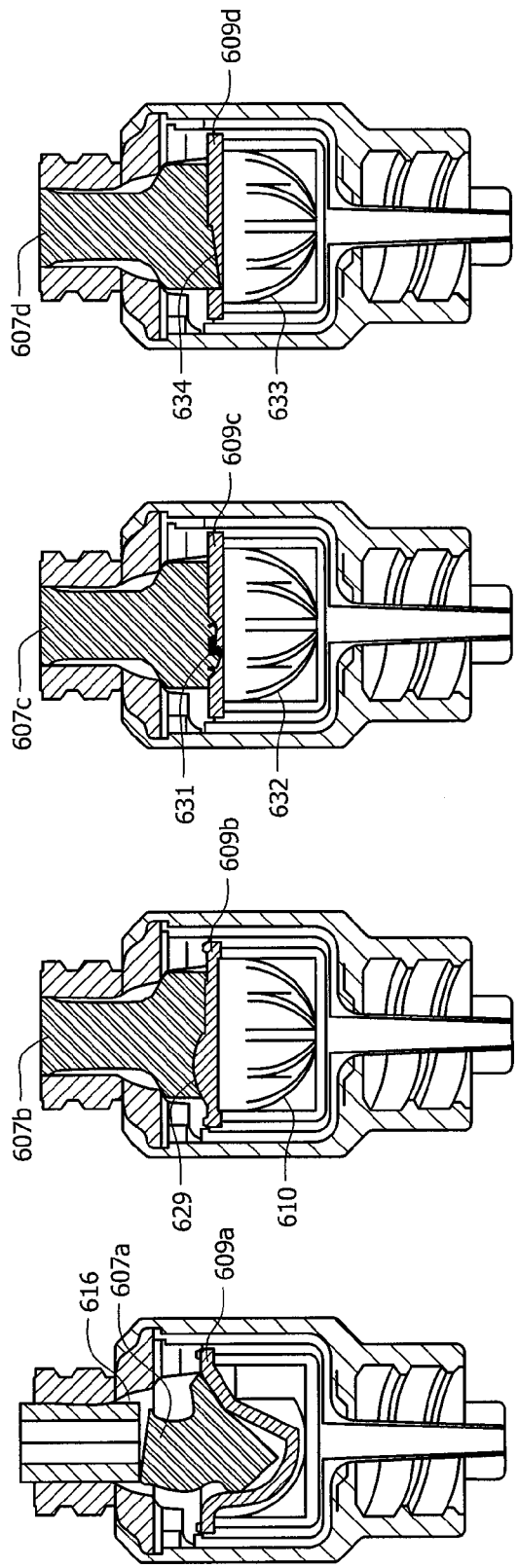

LUER ACTIVATED MEDICAL CONNECTOR HAVING A LOW PRIMING VOLUME

TECHNICAL FIELD

The present invention relates to medical connectors used in fluid delivery applications, and more specifically to connectors having a low priming volume and low positive displacement on disconnection.

BACKGROUND OF THE INVENTION

Medical connections are widely used in fluid delivery systems such as those used in connection with intravenous fluid lines, blood access, hemodialysis, peritoneal dialysis, enteral feeding, drug vial access, etc. Many prior art aseptic medical connections has been to puncture an elastomeric diaphragm or septum, which has one side in contact with the fluid, with a sharpened hollow hypodermic needle. The use of such hypodermic needles has been gradually decreasing as a result of both safety and cost considerations associated with infectious disease acquired from needle sticks. These connectors have been replaced with luer activated connectors which don't require hypodermic needles, but instead use an activator such as a luer on the end of a syringe or IV line to create a fluid path though a valve in a connector. The removal of the connector causes the valve to close when the line is disconnected. Such a system is described in U.S. Pat. No. 5,569,235 to Ross et al.

Typical connectors and valves of this type, such as described by Ross, have many attributes that are not ideal in medical applications for fluid delivery. First, such devices can have large priming volumes, that is the connector can have a large chamber associated with the valve element that must be filled with the fluid being delivered before that fluid is actually delivered into the patient line and the patient. For very low flow rates (for example, 0.1 milliliter per hour or 0.05 milliliters per hour), as is common for neonatal or infant care as well as other types of care, such a large priming volume can cause a delay of as much as several hours before the intended therapy reaches the patient. A connector having a low priming volume would allow an introduced therapy to reach the patient more quickly, even at low flow rates.

Second, fluid displacement can occur whenever a connection is made between two closed fluid systems. When a connection, such as a luer or hypodermic needle, is inserted into an intravenous connector or fluid tubing, fluid displacement occurs. Because the intravenous fluid is incompressible, a volume of fluid equal to the luer or needle volume is displaced out of the intravenous tubing and into the patient's blood vessel. This displacement of fluid from the intravenous tubing into the patient's blood vessel is referred to as antegrade flow. Similarly, when the connection is withdrawn, an equivalent volume of blood will be drawn back, usually through the catheter, into the intravenous tubing. This retrograde flow can be harmful when the blood drawn into the end of the catheter remains stagnant for a long period of time. The stagnant blood tends to settle, and may begin to clot, thereby restricting flow through the catheter and possibly requiring insertion of a new intravenous catheter into the patient. Connector systems providing for negative, or retrograde, displacement on insertion and positive, or antegrade flow on removal, are much more desirable in medical applications.

Third, most connectors use a septum, or permeable membrane at the connection site. These membranes must be penetrated on the insertion of the connector and therefore promote bacteria growth inside the connector. This septum is also susceptible to leaking when there is back pressure in the system. Connector systems that have swabable surfaces to allow for cleaning and which prevent leakage under backpressure are preferable.

BRIEF SUMMARY OF THE INVENTION

An embodiment of a connector is described having a valve housing defining an inlet port, and an outlet port, the valve housing further including a fluid path from the inlet port to the outlet port. The connector further includes a valve plug operable to seal the inlet port when the connector is in an unactuated state thereby closing the fluid path through the connector, and a diaphragm in the valve housing, the diaphragm separating the valve plug from an inner volume in the valve housing and the diaphragm sealing the inner volume, such that upon actuation of the connector the valve plug deforms the diaphragm into the inner volume thereby unsealing the inlet port and opening the fluid path through the connector.

A embodiment of a method of operating a connector for medical fluids is also described. The method includes actuating the connector by depressing a valve plug in the connector by inserting a male luer into an inlet port of the connector, the depressing of the valve plug opening a fluid path through the connector, deforming a diaphragm under pressure from the valve plug, the diaphragm defining and sealing an inner volume inside a valve housing of the connector, wherein the deformation of the diaphragm causes the connector to exhibit negative fluid displacement upon actuation, and closing the connector by removing the male luer from the inlet port, wherein the removal of the male luer causes the valve plug to reseal the connector and the diaphragm to return an undeformed state, wherein the return of the diaphragm to the undeformed state causes the connector to exhibit positive fluid displacement upon disconnection.

In another embodiment of the connector described herein, the connector includes a valve housing having a valve housing base and a valve cap, the valve housing defining an inlet port, and an outlet port, the valve housing further including a fluid path from the inlet port to the outlet port, the fluid path including a channel formed in an inner wall of the valve housing. The connector also includes a valve insert in the valve housing, the valve insert defining a bowl and a diaphragm in the valve housing and sealing the bowl of the valve insert, the sealed bowl forming an inner volume in the valve housing. A valve plug is operable to seal the inlet port when the connector is in an unactuated state thereby closing the fluid path through the connector, and wherein the diaphragm contacts the valve plug and applies a force to the valve plug to maintain the valve plug in the unactuated state. Upon actuation of the connector the valve plug deforms the diaphragm into the inner volume thereby unsealing the inlet port and opening the fluid path through the connector.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIGS. 5A through 5D are side views of the medical connector shown in FIG. 2, shown in various operational states; and FIGS. 6A through 6D are side views of the medical connector shown in FIG. 2, illustrating examples of various alternate embodiments.

DETAILED DESCRIPTION OF THE INVENTION

According to the concepts described herein, a needleless access medical device that combines, a low priming volume, positive displacement disconnection, and a swabable surface for disinfecting between uses is described.

Figure 1:
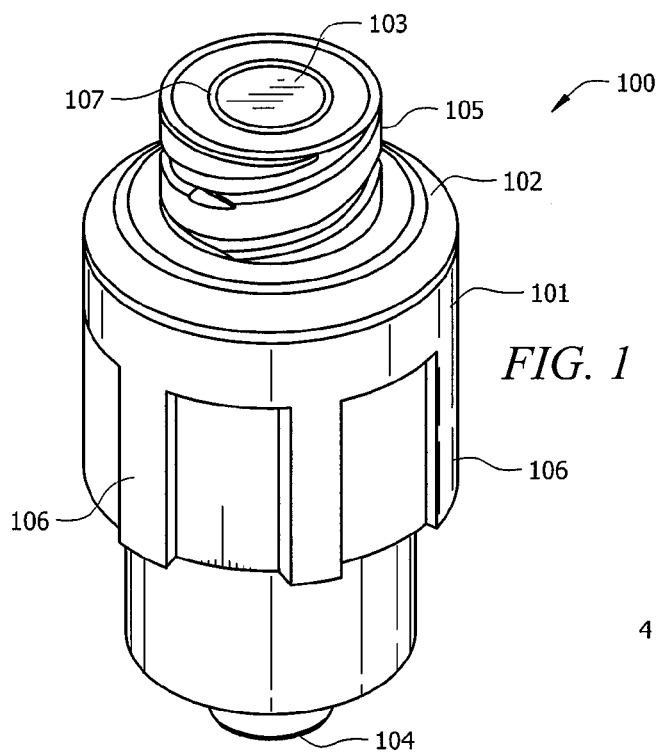
FIG. 1 is a perspective view of a luer activated medical connector in accordance with the concepts described herein.
Figure 2:
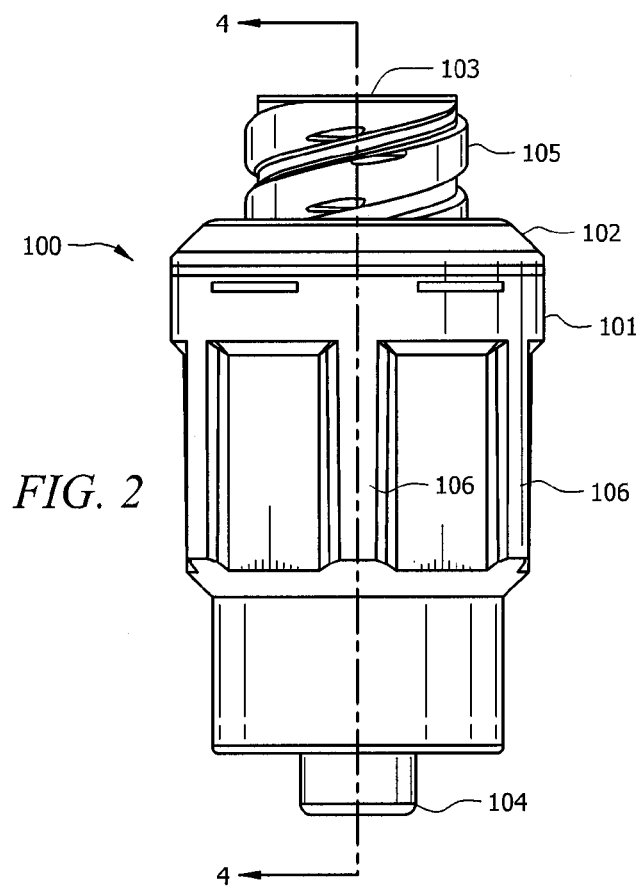
FIG. 2 is a side view of the medical connector shown in FIG. 1.

Turning to FIGS. 1 and 2, an embodiment of a low priming volume luer activated connector 100 according to the concepts described herein is shown in perspective view and side view respectively. The luer activated connector 100 is formed by valve housing 101 and a valve cap 102. Valve cap 102 is secured to the valve housing 101 using conventional means, such as solvent bonding, ultrasonics, spin welding, etc. A valve inlet port 103 is sealed by the top of valve plug 107 which forms a swabable surface that can be cleaned between uses. Valve inlet port 103 accepts an actuator which pushes valve plug 107 into valve housing 101 to create a fluid path through connector 100 as will be described below. Valve inlet port 103 includes threads which allow connector 100 to be securely connected to a syringe or other fluid dispensing mechanism.

Housing ribs 106 provide structural support to valve housing 101 and also provide for gripping surfaces to allow connector 100 to be held firmly while attaching another device. As will be described below in a preferred embodiment a channel is formed on the interior of one of the ribs to provide a low priming volume fluid path through connector 100. Actuator 104 allows the connector to be connected to the inlet port of another device, such as a IV tube or manifold.

Figure 3:
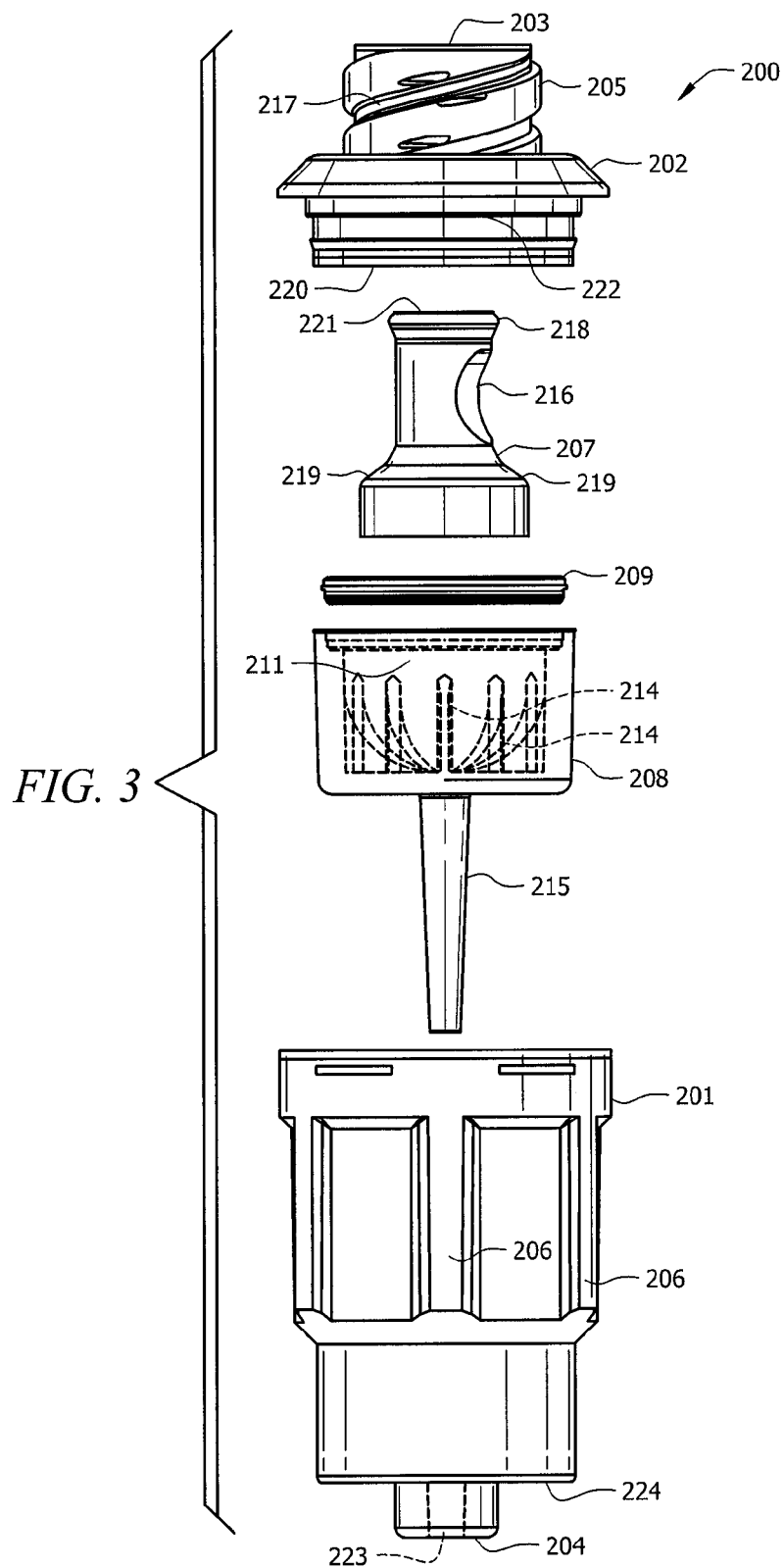
FIG. 3 is a is a exploded side view of the medical connector shown in FIG. 2.

Referring now to FIG. 3, an embodiment of connector 200 according to the concepts described herein is shown in an exploded side view illustrating the various components of connector 200. The embodiment of connector 200 shown herein includes valve housing 201, valve cap 202, valve plug 207, valve insert 208, and diaphragm 209. As described with respect to FIGS. 1 and 2, valve cap 202 has inlet port 203 with threads 205 which receives an actuator from a fluid dispensing or other device. Internal chamber 222 is formed by valve cap 202 and valve housing 201 when mated together and is designed to receive valve plug 207.

Valve plug 207 is of a generally cylindrical shape for slidably fitting within internal chamber 222 formed by valve cap 202 and valve housing 201. Valve plug includes a primary shoulder seal 219 adapted for abutting against the valve seat 220 of the valve cap 202. Valve plug 14 also includes wiping seal 218 which engages the internal surface of the throat 217 of valve cap 202. As will be described below, wiping seal 218 acts to remove any fluid from the throat 217 of valve cap 202 when an actuator is disengaged from connector 200. Valve plug 207 may also include notch 216. Notch 216 facilitates the deformation of valve plug 207 when under pressure from a luer actuator. The deformation of valve plug 207 creates a fluid path through connector 200.

Preferred embodiments of connector 200 also include valve insert 208 and diaphragm 209. Valve insert 208 includes bowl 211. When diaphragm 209 is mated with valve insert 208 an air pocket in formed in bowl 211. The air pocket in bowl 211 provides a counter pressure to diaphragm 209 during fluid flow and works to ensure a negative fluid displacement during insertion and a positive fluid displacement during disconnection as will be explained. Support ribs 214 provide structural rigidity to valve insert 208 and help support diaphragm 209 the air pocket of bowl 211 when the diaphragm in an extended or stretched position.

Valve insert 208 and diaphragm 209 perform several functions in connector 200. First, they occupy space that would otherwise be filled by fluid, thereby minimizing the priming volume required to achieve fluid flow through connector 200. Second, they provide the mechanism by which connector 200 achieves the proper fluid flow characteristics, namely positive fluid displacement during disconnection. Further, diaphragm 209 deforms under back pressure in the system, deforming to accept fluid inserted into the connector during back pressure and then positively displacing that fluid out of the connector when the back pressure has subsided. Bowl 211 also provides a volume for valve plug 207 to displace into when valve plug 207 is displaced by an actuator inserted into inlet port 203. Diaphragm 209 stretches into bowl 211 under the force of valve plug 207, but only to the extent necessary, thereby minimizing priming volume. Diaphragm 209 also provide a counter force against valve plug 207, helping to push valve plug 207 back into chamber 222 when the actuator is removed, thereby resealing inlet port 203 of connector 200.

Stem 215 of valve insert 208 extends into outlet port 223 of valve housing 201 further decreasing the internal volume of connector 200 and thereby minimizing the priming volume for fluids flowing through connector 200. Valve insert 208 slides tightly into valve housing 201 creating a tight connection between the external walls of valve insert 208 and the internal walls of valve housing 201. A single flow channel is impeded into one of the ribs 206 on the internal side wall of valve housing 201 and also on the base wall of housing 201. Stem 215 is sized such that when inserted into the outlet port 223 of connector 200, the cross sectional flow volume of outlet port 223 will be equivalent to the flow volume through the channel in the side wall of valve housing 201.

Valve housing 201 also includes male luer 204 and female threads 224. The connection creatable by male luer 204 and threads 224 is a standardized connection common to medical fluid delivery devices and is the counterpart to the connection formed by the inlet port 203 and male threads 205.

Figure 4:
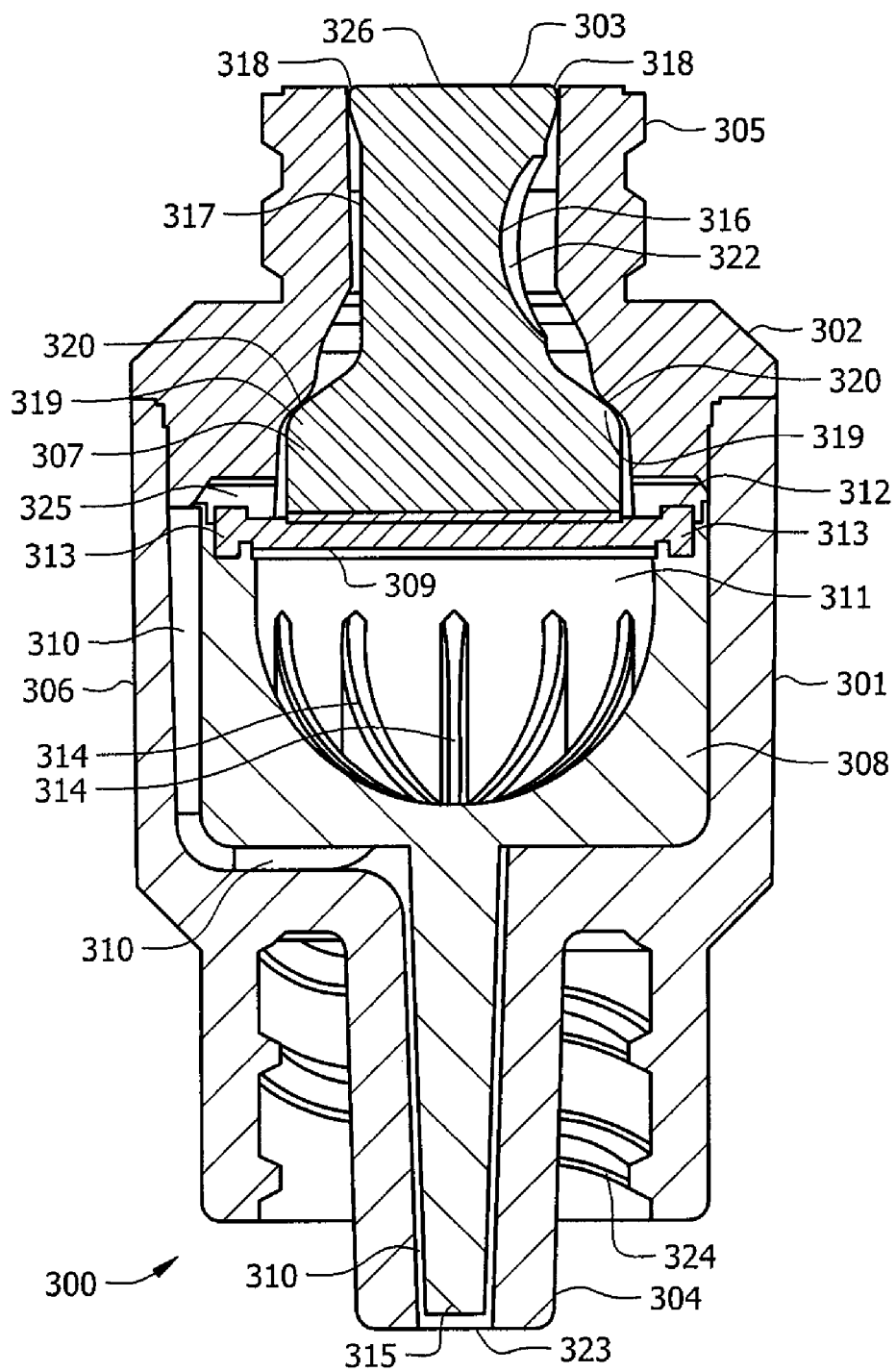
FIG. 4 is a is a section view of the medical connector shown in FIG. 2.

Referring now to FIG. 4, a cross-section of an embodiment of connector according to the concepts described herein is shown assembled. A preferred embodiment of connector 300 again includes valve housing 301, valve cap 302, valve insert 308, valve plug 307 and diaphragm 309. Valve insert 308 and diaphragm 309 fit tightly into valve housing 301 and held in place by valve cap 302 which is securely attached to valve housing 301 by welding or other means. A flange 313 on diaphragm 309 fits into a grove 312 created by valve cap 302 and valve insert 308. Flange 313 and groove 312 hold diaphragm 309 securely in place and prevent diaphragm 309 from moving when it deforms into bowl 311.

Valve plug 307 fits into chamber 322 formed when valve cap 302 is fitted to valve housing 301 with valve insert 308 and diaphragm 309 inserted. In the closed position shown, shoulder seal 319 of valve plug 307 abuts tightly against the valve seat 320 preventing any fluid flow though connector 300. Additionally, wiping seal 318 seals the entrance to inlet port 303 by providing a seal around the internal wall of throat 317 of valve cap 302. Wiping seal 318 also acts to remove any fluid from the throat 317 by forcing any fluid in throat 317 up and out of connector 300 when valve plug 307 transitions from an open position to the closed position shown in FIG. 4. Notch 316 of valve plug 307 is used to control the deformation of valve plug 307 under pressure from an actuator (not shown) inserted into connector 300.

Though the connector 300 is shown in the closed position in FIG. 4 with the top portion of the fluid path closed by wiping seal 318 and particularly by shoulder seal 319, the lower portion of the fluid path 310 through connector 300 is shown. Fluid path 310 includes chamber 325 formed by open portion of valve cap 302 and diaphragm 309. Chamber 325 is in communication with the channel impeded in one of the ribs 306 of valve housing 301. While connector 300 is shown with a single channel fluid path, channels in other ribs of valve housing 301 may be used in connector 300 to increase flow volume. Also the size of the channel for fluid path 310 can be altered to alter the flow characteristics of the device. It should be noted that increasing channel size or adding additional channels could increase the priming volume of the device.

The fluid path 310 continues from the channel in rib 306 into a channel in the base of valve housing 301. The fluid path then enters outlet port 323 in male luer 304 of valve housing 301. Stem 315 is sized such that the remaining open space in outlet port 323 is matched to the flow characteristics of fluid path 310 through the rest of valve housing 301. As stated, stem 315 occupies space in outlet port 323 that would otherwise be part of the priming volume for connector 300.

Male luer 304 of valve housing 301 allows connector 300 to be inserted into another device such as a manifold, IV line connector or any other device with a universal type female connector. Threads 324 allow connector 300 to be secured in place when connected via male luer 304. As described, top surface 326 of valve plug 307 sits flush with the top of valve cap 302, and wiping seal 318 removes fluids from inlet port 303 of connector 300 when the connector is disengaged from another device. This arrangement provides connector 300 with a swabbable inlet surface that can be cleaned and disinfected between uses. Other connector devices that use a slit in a septum allow fluids to collect underneath the septum and are not able to be easily disinfected between uses.

During use the male luer portion of another device forces valve plug down into connector 300. Diaphragm 309 is deformed into bowl 311 by valve plug 307 and shoulder seals 319 separates from valve seat 320, thereby opening fluid path 310 through connector 300. Notch 316 in valve plug 307 controls the deformation of valve plug 307 and allows it to fold down into connector 300 ensuring that valve plug 307 depresses far enough into connector 300 to allow a good connection with the device being inserted. Diaphragm 309 and the air pocket in bowl 311 provide a positive pressure on valve plug 307, thereby ensuring that valve plug 307 reseats property upon removal of the actuating device.

Further, upon actuation the depression of valve plug 307 on diaphragm 309 creates a larger open volume inside connector 300 thereby drawing downstream fluid into connector 300 providing the desired negative displacement on connection. The return of the valve plug 307 and diaphragm 309 back into the unextended position after disconnection reduces the internal volume of connector 300. As shoulder seal 319 of valve plug 307 prevents fluid from being pushed out inlet port 303, the fluid in bowl 311 is pushed out outlet port 323 upon removal of the actuating device, thereby providing the desired positive displacement on disconnection.

With the internal volume of connector 300 being occupied by valve insert 308, diaphragm 309 and valve plug 307, it can be easily seen that the internal volume, which is also the priming volume of connector 300, is minimized. Minimizing priming volume can be important in a variety of applications, but can be particularly important in applications involving low dose medications or in neonatal applications where very low flow rates are maintained. In preferred embodiments of a connector according to the concepts described herein, a low priming volume could be considered a priming volume of 70 microliters or less, though greater priming volumes may be appropriate for other applications while remaining within scope of the concepts described herein.

Referring now to FIGS. 5A through 5D, various aspects of a preferred embodiment of a connector 400 are described. Each of the connectors shown includes a valve housing 401, a valve cap 402, a valve plug 407, a valve insert 408 and a diaphragm 409 as described with respect to FIGS. 1 through 4.

FIG. 5A shows connector 400 in its closed position with valve plug 407 sealing connector 400 and preventing any fluid from passing through the connector. Diaphragm 409 is in its normal condition for a closed configuration. FIG. 5B illustrates the portion of fluid path 410 after valve plug 407. As valve plug 407 is in its closed position the fluid path is closed by the valve plug as described with respect to FIG. 4.

FIG. 5C shows connector 400 under back pressure through outlet port 423. Fluid entering outlet port 423 travels along fluid path 410 shown in FIG. 5B and is blocked by valve plug 407 from exiting connector 400. Instead the fluid causes diaphragm 409 to expand into bowl 411 creating a space for a volume of fluid between valve plug 407 and diaphragm 409. Additionally, valve plug 407 is held in place by the back pressure, thereby reinforcing the seals between valve plug 407 and valve cap 402 and ensuring that connector 400 does not leak under back pressure conditions. When the back pressure condition ends the elasticity of diaphragm 409 and the pressure from the air pocket in bowl 411 force the fluid that entered the connector under back pressure to exit through outlet port 423.

FIG. 5D shows connector 400 in an open or actuated state with a male luer compressing valve plug 407 into the body of connector 400. Valve plug 407 causes diaphragm 409 to expand into bowl 411 creating space for valve plug 407 and opening the fluid path through the device. Diaphragm 409 and the mass of valve pug 407 minimize the volume inside connector 400 in the actuated state, thereby minimizing the priming volume required by connector 400.

Referring now to FIGS. 6A through 6D, various alternative embodiments of the valve plug and diaphragm in a connector are described. Each of the connectors shown includes operates essentially as described with respect to FIGS. 1 through 5.

FIG. 6A shows a notched valve plug 609a in its actuated state with diaphragm 609a in its expanded state as described above. The notch allows valve plug 607a to deform in a desired manner upon actuation by a male luer. FIG. 6B shows a diaphragm 609b having a dimple 630 and a corresponding recess 629 in valve plug 607b. The dimple and recess again allow diaphragm 609b and valve plug 607b to deform in a desired manner.

FIG. 6C shows a diaphragm 609c having a recess 632 and a corresponding dimple 631 in valve plug 607c. As before, the dimple and recess allow diaphragm 609c and valve plug 607c to deform in a desired manner. FIG. 6D shows a diaphragm 609d having a notch 633 and a corresponding slant 634 in valve plug 607d. The slant and notch allow diaphragm 609d and valve plug 607d to deform in a desired manner. While certain alternate embodiments have been explicitly shown, one skilled in the art would understand that many other alternate embodiments could be envisioned that would have the same or similar function and still be well within the scope of the concepts described herein.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A connector comprising:
   a valve housing comprising an inlet port, an outlet port, an inner wall, and one or more channels in the inner wall forming a fluid path from the inlet port to the outlet port;
   a valve plug operable to seal the inlet port when the connector is in an unactuated state thereby closing the fluid path through the connector;
   a diaphragm disposed within the valve housing; and
   a valve insert disposed within the valve housing, the valve insert comprising a bowl sealed by the diaphragm forming an inner volume, the valve insert further comprising a stem extending into the outlet port, the stem configured such that a cross-sectional flow area of the outlet port is approximately equivalent to a cross-sectional flow area of the flow path formed by the one or more channels in the inner wall of the valve housing;
   wherein upon actuation of the connector the valve plug deforms the diaphragm into the inner volume thereby unsealing the inlet port and opening the fluid path through the connector.

2. The connector of claim 1 wherein the valve housing is formed by a valve housing base and a valve cap.

3. The connector of claim 1 wherein the inlet port of the valve housing includes a neck portion, and the valve plug includes a wiping seal such that the wiping seal of the valve plug forces fluid in the neck portion of the inlet port out of the connector when the connector is transitioned from an unactuated state to an actuated state.

4. The connector of claim 1 wherein the connector exhibits negative displacement of fluid upon actuation.

5. The connector of claim 1 wherein the connector exhibits positive displacement of fluid when the connector is transitioned from an actuated state to an unactuated state.

6. The connector of claim 1 wherein the sealed inner volume of the valve housing results in a low priming volume for the connector.

7. The connector of claim 1, wherein the connector has a priming volume equal to or less than 70 microliters.

8. The connector of claim 1 wherein a top surface of the valve plug comprises a swabbable surface.

* * * * *